United States Patent [19]
Wang et al.

[11] Patent Number: 5,319,127
[45] Date of Patent: Jun. 7, 1994

[54] PHENOLIC-HYDRAZIDE COMPOUNDS AND POLYOLEFIN COMPOSITIONS STABILIZED THEREWITH

[75] Inventors: Richard H. S. Wang; Ping P. Shang; Daniel A. Jervis, all of Kingsport, Tenn.

[73] Assignee: Eastman Chemical Company, Kingsport, Tenn.

[21] Appl. No.: 125,392

[22] Filed: Sep. 23, 1993

Related U.S. Application Data

[63] Continuation-in-part of Ser. No. 858,809, Mar. 27, 1992.

[51] Int. Cl.$^5$ .............................................. C07C 69/76
[52] U.S. Cl. ...................... 560/75; 525/296; 427/259; 427/264
[58] Field of Search ........................... 560/75; 525/296

[56] References Cited

U.S. PATENT DOCUMENTS

| | | | |
|---|---|---|---|
| 3,772,245 | 11/1973 | Dexter | 260/45.85 |
| 4,093,774 | 6/1978 | Hartless et al. | 428/379 |
| 4,147,689 | 4/1979 | Thompson et al. | 260/45.9 |

FOREIGN PATENT DOCUMENTS

| | | |
|---|---|---|
| 1267839 | 5/1968 | Fed. Rep. of Germany . |
| 2376129 | 7/1978 | France . |

OTHER PUBLICATIONS

Chemical Abstracts 111:196063a, an abstract of Japanese Kokai 01 38, 453 [89 38,453] published Feb. 8, 1989.
Chemical Abstracts 114:83269r, an abstract of Japanese Kokai 02,214,751 [90,214,751] published Aug. 27, 1990.
Chemical Abstracts 111:175288n, an abstract of Polym. Degrad. Stab. 1989, 25(1), 19–29.

*Primary Examiner*—Paul J. Killos
*Attorney, Agent, or Firm*—J. Frederick Thomsen; William P. Heath, Jr.

[57] ABSTRACT

Disclosed are a class of phenolic-hydrazide compounds of diverse structure which are useful as stabilizers for polyolefins. The phenolic-hydrazide compounds inhibit oxidative degradation of polyolefins which is attributable to heat and/or ultraviolet light and is promoted or accelerated by metals, e.g., copper, in contact with the polyolefin.

10 Claims, No Drawings

PHENOLIC-HYDRAZIDE COMPOUNDS AND POLYOLEFIN COMPOSITIONS STABILIZED THEREWITH

This application is a continuation in part of our U.S. patent application Ser. No. 07/858,809 filed Mar. 27, 1992.

This invention pertains to certain novel phenolic-hydrazide compounds which are useful as metal deactivators and antioxidants in polyolefins. This invention also pertains to polyolefin compositions containing one or more of the phenolic-hydrazide compounds.

Poly-α-olefins require the presence therein of stabilizers to prevent or retard oxidative, thermal and/or ultraviolet light deterioration. The most common of such poly-α-olefins are low, medium and high density polymers derived from ethylene, propylene, mixtures thereof and copolymers of ethylene and minor amounts of higher α-olefins such as 1-butene, 1-hexene, 1-octene, 1-dodecene, etc. Stabilizers typically present in such poly-α-olefins include a phenolic antioxidant such as 2,2-bis[[3-[3,5-bis(2-methyl [-2-propyl)-4-hydroxyphenyl]-1-oxopropoxy]methyl]-1,3 propanediyl 3,5-bis(1,1-dimethyl)-4-methylethyl)-4-hydroxybenzenepropanoate (Irganox 1010 stabilizer) or 2,6 bis(1-methylheptadecyl)-p-cresol, phosphites such as trihydrocarbyl phosphites including cyclic phosphites and sulfides such as thiodipropionate esters such as dilauryl thiodipropionate.

When poly-α-olefin compositions are used as coatings for metals, e.g., as wire coating compositions, the compositions also contain a metal deactivator to inhibit polymer degradation which is promoted or accelerated by the metal. For example, polyolefin compositions used to coat copper wire typically contain a copper deactivator such as N,N'-dibenzaloxalyldihydrazide. For some wire coating applications, it is necessary that the metal deactivator resist leaching from the polyolefin when it is in contact with such materials as petrolatum used as a filler in electrical cables. However, most commercial phenolic antioxidants such as Irganox 1010 are readily leached from the polyolefin coating by petrolatum.

One embodiment of the present invention pertains to a class of novel phenolic hydrazide compounds which function as both phenolic antioxidants and metal deactivators when incorporated into poly-α-olefins intended for use in coating metal articles, particularly copper wire. These novel compounds have the general formula:

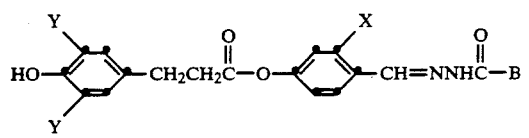   (I)

wherein
B is a group having the formula

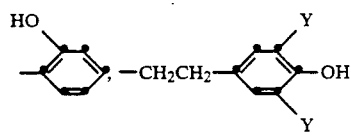

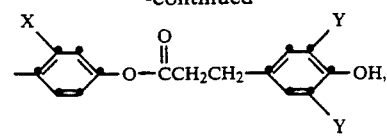

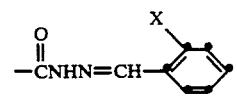

or

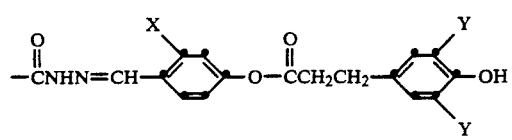

X is hydrogen or hydroxyl; and
Y is a tertiary hydrocarbyl group having the formula

wherein Z is alkyl or aryl.

Examples of the alkyl groups represented by Z include alkyl containing up to about 8 carbon such as methyl, ethyl, propyl, 2 propyl, butyl, 2 butyl, 2 methyl 2-propyl, pentyl, 2 pentyl, hexyl, 2 ethyl hexyl, 2,4,4-trimethyl-2 pentyl. The alkyl groups preferably contain up to 4 carbon atoms. The aryl group represented by Z may be unsubstituted phenyl or phenyl substituted with 1 or 2 groups selected from lower, i.e., containing up to about 4 carbon atoms, alkyl, lower alkoxy or halogen, e.g., chlorine or bromine. Z most preferably is methyl, i.e., the hydrocarbyl group represented by Y is 2 methyl 2 propyl (tertiary butyl).

A second embodiment of the invention pertains to a polyolefin composition comprising an intimate mixture of (i) a normally solid polymer of ethylene, propylene, a mixture of ethylene and propylene or polymers of ethylene and an α-olefin having 4 to 12 carbon atoms and (ii) 1 or more compounds of formula (I) above. The concentration of the compound of formula (I) which will effectively inhibit polymer degradation can vary considerably depending on the particular polymer being stabilized and the end use for which the stabilized polymeric material is designed. Generally, concentrations in the range of 0.05 to 5.0 weight percent may be used with concentrations of about 0.1 to 1.0 being most common. The stabilizers provided by this invention may be used in combination with other conventional stabilizers such as polyvalent salts of organic acids, thioethers, phosphites and ultraviolet light stabilizers. In addition, other additives, such as plasticizers, lubricants, emulsifiers, antistatic agents, flame retardant agents, pigments and fillers, commonly used in formulating commercial polymeric compositions may be present.

The novel stabilizer compounds of formula (I) provided by the present invention may be prepared in accordance with conventional synthesis procedures by reacting an aryl aldehyde having the formula

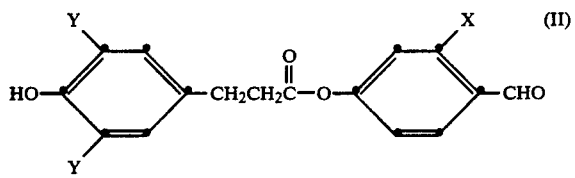

with a hydrazide compound having the formula

wherein B and X are defined hereinabove. The intermediates of formulas (II) and (III) are known compounds and/or can be prepared according to procedures generally known in the art.

The preparation of the stabilizers of the invention is further illustrated by the following examples.

EXAMPLE 1

A mixture of 3- [4-hydroxy-3,5-bis(2-methyl-2-propyl) phenyl]propionyl chloride (0.15 mol), 4-hydroxybenzaldehyde (0.135 mol), pyridine (17 mL) and methylene chloride (350 mL) is heated at reflux (40° C) for 24 hours, cooled and washed with water until neutral. Evaporation of the methylene chloride solvent gave the aldehyde product having the structure:

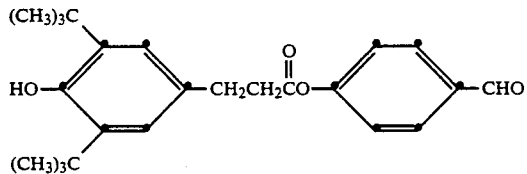

The aldehyde (0.23 mol) prepared as described in the preceding paragraph and oxalyl dihydrazide (0.1115 mol) are reacted as described in Example I to obtain 88 g of product having a melting point of 280 285° C. and the structure:

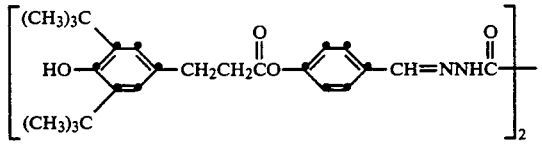

EXAMPLE 2

The general procedure of Example 1 is repeated except that an equivalent amount of 2,4 dihydroxybenzaldehyde is substituted for the 4-hydroxybenzaldehyde. The product thus obtained, after recrystallization from 2-propanol, has a melting point greater than 160° C. and the structure:

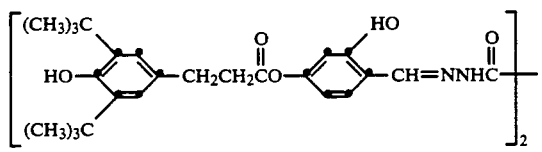

EXAMPLE 3

The general procedure of Example 1 is repeated except that an equivalent amount of salicyl hydrazide is substituted for the oxalyl dihydrazide. The product thus obtained has a melting point of 194-198° C. and the structure:

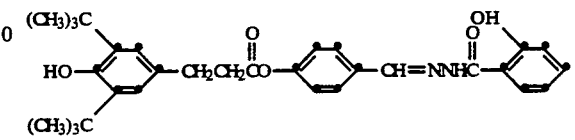

EXAMPLE 4

The general procedure of Example 2 is repeated except that an equivalent amount of salicyl hydrazide is substituted for the oxalyl dihydrazide. The product thus obtained has a melting point of 200-210° C. and the structure:

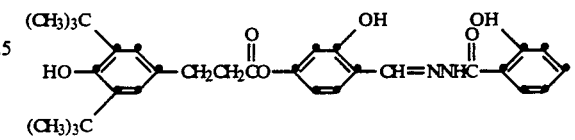

EXAMPLE 5

The general procedure of Example 1 is repeated except that an equivalent amount of 3- [4-hydroxy-3,5-bis(2-methyl-2-propyl)phenyl]propionyl hydrazide is substituted for the oxalyl dihydrazide. The product thus obtained has a melting point of 174-178° C. and the structure:

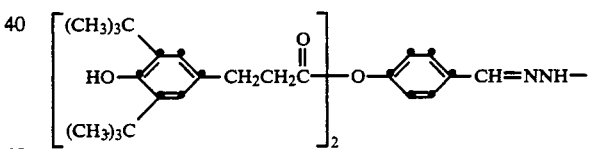

EXAMPLE 6

The general procedure of Example 2 is repeated except that an equivalent amount of 3-[4-hydroxy-3,5-bis(2-methyl 2-propyl)phenyl]propionyl hydrazide is substituted for the oxalyl dihydrazide. The product thus obtained has a melting point of 135 -150° C. and the structure:

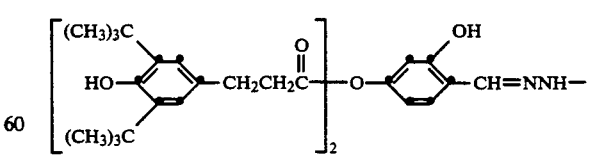

The polyolefin compositions provided by the present invention may be prepared by incorporating one or more of the phenolic hydrazide described hereinabove into poly-α-olefin polymers by conventional blending techniques. For example, the phenolic hydrazide compounds may be added directly to a melt of the polyolefin on a roll mill to distribute the phenolichydrazide compound uniformly throughout the polymer. Alternatively, the compounds may be dry blended with a finely-divided form of the polyolefin such as pellets and then the dry mix can be mixed further in and extruded from an extruder.

The novel polyolfin compositions of the invention are particularly useful for coating copper materials such as copper wires. Thus, a third embodiment of the present invention pertains to a coated article comprising a copper material, especially copper wire, bearing a coating of one of the polyolefin compositions described herein.

EXAMPLES 7–12 AND COMPARATIVE EXAMPLE 1

The phenolic hydrazide compounds prepared as described in Examples 1, 2 and 4–6 hereof are evaluated as stabilizers in and for polyethylene according to the following procedure. The amounts of materials employed are given in parts by weight. Each phenolic hydrazide compound (1.2 parts) is dry mixed with a sample (600 parts) of unstabilized, high density polyethylene (Alathon 7050, Oxy Chemical). Each mixture then is fed to and extruded from a C. W. Brabender conical, twin-screw extruder at 200° C. over a period of 2 minutes. Each extruded polyolefin composition is pelletized and the pellets are pressed into film 254 microns thick at a temperature of 200° C. and a pressure of 68.95 megapascals (10,000 pounds per square inch) using a Carver laboratory press. Film also was prepared from the same high density polyethylene which did not contain any phenolic-hydrazide compound.

The stability of the film samples of the polyolefin compositions is determined by Differential Scanning Calorimetry (DSC) analysis according to the general procedure described by Ellerstein, "The Use of Dynamic Differential Calorimetry for Ascertaining the Thermal Stability of Polymers," Analytical Calorimetry, Eds., R.S. Porter and J.F. Johnson, Plenum, New York, 1968, p. 279 and by Wright, "Oxidative Stability of Expanded Polyethylene for Wire and Cable," J. Cell. Plast., 6, 317 (1976). A 3–4 mg sample of each film is placed in an aluminum or copper pan Without the lid and scanned at a rate of 20° C. per minute from 40 to 300° C. under forced air at a rate of 15 mL per minute. Degradation of a polyolefin composition occurs at the temperature at which an oxidative exotherm is observed. The thermal oxidative degradation of polyolefins is essentially a controlled burning and thus produces heated which is detected by the DSC instrument. A stabilizer which increases the temperature at which degradation begins increases the overall usefulness of the polyolefin. The onset temperature of the oxidative exotherm curve that is measured as the degradation temperature of a sample is determined as the intercept of the baseline before degradation starts and the following straight line when degradation occurs.

The temperature at which each polyolefin composition degrades, determined as described above, is shown in Table I. Degradation temperatures are given in Table I for the film samples scanned in the aluminum pan and the copper pan. It is apparent from the examples of Table I, including Comparative Example I (C I), that the copper of the copper pan promotes or accelerates the degradation of the film samples of the polyolefin compositions It also is apparent that the presence of one of the phenolic hydrazide compounds of the present invention in the polyethylene improves the stability thereof by raising the temperature at which the polyolefin composition degrades, as determined in both the aluminum (Al) pan and in the copper (Cu) pan.

TABLE I

| Example | Polyolefin Composition Containing Compound of Example: | Degradation Temperature, °C. Al Pan | Degradation Temperature, °C. Cu Pan |
|---|---|---|---|
| C-1 | None | 239 | 220 |
| 8 | 1 | 252 | 251 |
| 9 | 2 | 261 | 256 |
| 10 | 4 | 251 | 241 |
| 11 | 5 | 262 | 253 |
| 12 | 6 | 262 | 251 |

The invention has been described in detail with particular reference to preferred embodiments thereof, but it will be understood that variations and modifications may be effected within the spirit and scope of the invention.

We claim:

1. A compound having the formula:

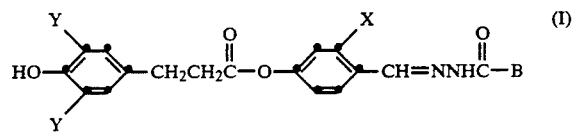

wherein
B is a group having the formula

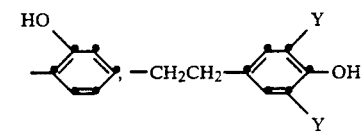

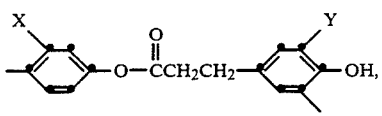

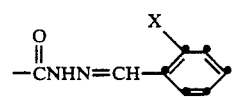

or

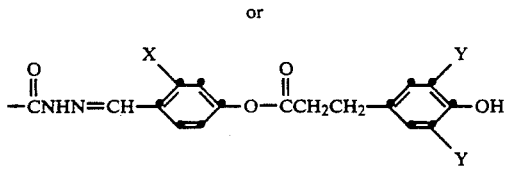

X is hydrogen or hydroxyl; and
Y is a tertiary hydrocarbyl group having the formula

wherein Z is alkyl or aryl.

2. A compound according to claim 1 having the formula:

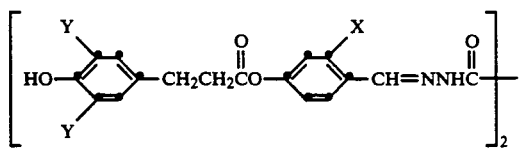

wherein
X is hydrogen or hydroxyl; and
Y is a tertiary hydrocarbyl group having the formula

wherein Z is alkyl or aryl.

3. A compound according to claim 1 having the formula:

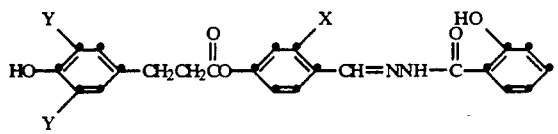

wherein
X is hydrogen or hydroxyl; and
Y is a tertiary hydrocarbyl group having the formula

wherein Z is alkyl or aryl.

4. A compound according to claim 1 having the formula:

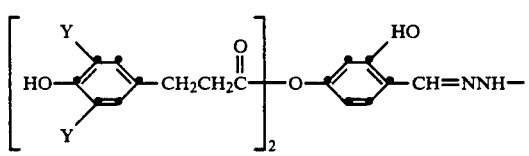

wherein
X is hydrogen or hydroxyl; and
Y is a tertiary hydrocarbyl group having the formula

wherein Z is alkyl or aryl.

5. A polyolefin composition comprising an intimate mixture of
(i) a normally solid polymer of ethylene, propylene, a mixture of ethylene and propylene or polymers of ethylene and an α-olefin having 4 to 12 carbon atoms; and (ii) a compound having the formula:

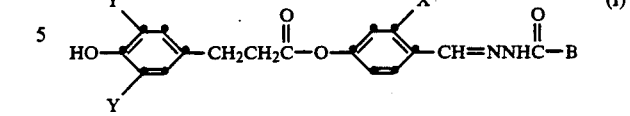

wherein
B is a group having the formula

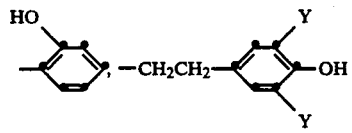

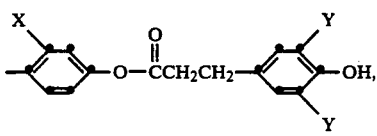

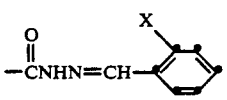

or

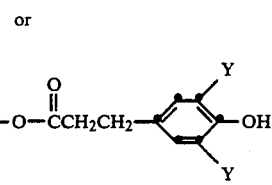

X is hydrogen or hydroxyl; and
Y is a tertiary hydrocarbyl group having the formula

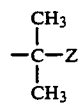

wherein Z is alkyl or aryl.

6. A composition according to claim 5 wherein component (i) is polyethylene and the concentration of component (ii) is about ? .1 to 1.0 weight percent based on the total weight of the composition.

7. A composition according to claim 5 wherein component (ii) is a compound having the formula:

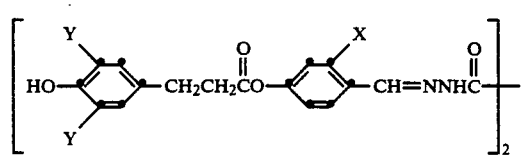

wherein
X is hydrogen or hydroxyl; and
Y is a tertiary hydrocarbyl group having the formula

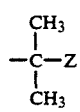

wherein Z is alkyl or aryl.

8. A composition according to claim 5 wherein component (ii) is a compound having the formula:

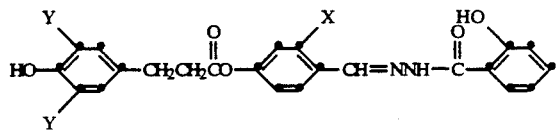

wherein
X is hydrogen or hydroxyl; and
Y is a tertiary hydrocarbyl group having the formula

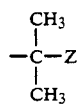

wherein Z is alkyl or aryl.

9. A composition according to claim 5 wherein component (ii) is a compound having the formula:

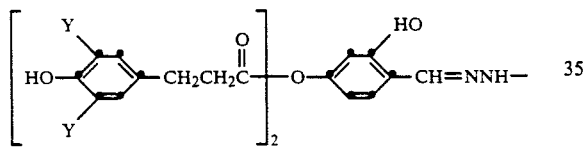

wherein
X is hydrogen or hydroxyl; and
Y is a tertiary hydrocarbyl group having the formula

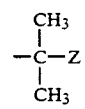

wherein Z is alkyl or aryl.

10. A coated article comprising a copper material bearing a coating of a polyolefin composition comprising
(i) a normally solid polymer of ethylene, propylene, a mixture of ethylene and propylene or polymers of ethylene and an α-olefin having 4 to 12 carbon atoms; and
(ii) a compound having the formula:

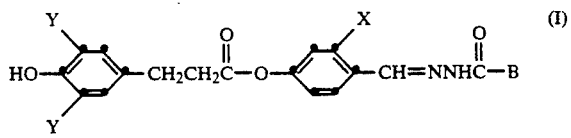

wherein
B is a group having the formula

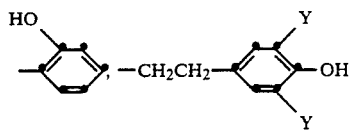

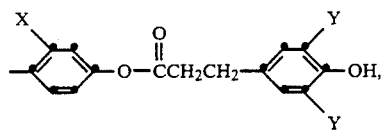

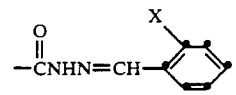

or

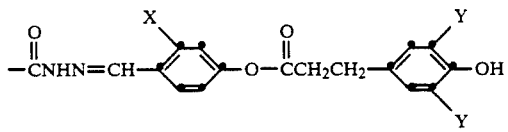

X is hydrogen or hydroxyl; and
Y is a tertiary hydrocarbyl group having the formula

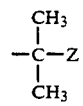

wherein Z is alkyl or aryl.

* * * * *